(12) United States Patent
Yu et al.

(10) Patent No.: US 7,442,240 B2
(45) Date of Patent: Oct. 28, 2008

(54) ALKOXYLPROPYLISOTHIAZOLINONE AND PREPARATION METHOD AND USE THEREOF

(75) Inventors: Liangmin Yu, Qingdao (CN); Xiaohui Jiang, Qingdao (CN); Zhiming Zhang, Qingdao (CN); Huanzhi Xu, Qingdao (CN); Changcheng Li, Qingdao (CN)

(73) Assignee: Ocean University of China, Shinan District, Qingdao, Shandong, P.R. (CN)

( * ) Notice: Subject to any disclaimer, the term of this patent is extended or adjusted under 35 U.S.C. 154(b) by 0 days.

(21) Appl. No.: 11/664,717

(22) PCT Filed: Sep. 30, 2005

(86) PCT No.: PCT/CN2005/001629

§ 371 (c)(1),
(2), (4) Date: May 1, 2007

(87) PCT Pub. No.: WO2006/037274

PCT Pub. Date: Apr. 13, 2006

(65) Prior Publication Data

US 2007/0256596 A1    Nov. 8, 2007

(30) Foreign Application Priority Data

Oct. 10, 2004  (CN) ................ 2004 1 0035958
Oct. 16, 2004  (CN) ................ 2004 1 0035989
Oct. 16, 2004  (CN) ................ 2004 1 0035990

(51) Int. Cl.
*A01N 43/80* (2006.01)
*C07D 275/03* (2006.01)
*C09D 5/16* (2006.01)

(52) U.S. Cl. ............ 106/18.33; 106/15.05; 424/78.09; 424/405; 514/372; 523/122; 523/177; 548/213

(58) Field of Classification Search ............ 106/15.05, 106/18.33; 424/78.09, 405; 514/372; 523/122, 523/177; 548/213
See application file for complete search history.

(56) References Cited

U.S. PATENT DOCUMENTS

| 3,523,121 A | * | 8/1970 | Law et al. ............... 548/213 |
| 3,761,488 A | | 9/1973 | Lewis et al. |
| 4,105,431 A | * | 8/1978 | Lewis et al. ............. 504/156 |
| 5,142,058 A | | 8/1992 | Willingham et al. |
| 5,498,344 A | * | 3/1996 | Rei et al. ................ 252/404 |
| 5,554,635 A | * | 9/1996 | Rei et al. ................ 514/372 |
| 2006/0293374 A1 | * | 12/2006 | Beers ..................... 514/372 |

FOREIGN PATENT DOCUMENTS

| CN | 1042350 | 5/1990 |
| CN | 1042350 A | 5/1990 |
| CN | 1055282 | 10/1991 |
| JP | 8-020676 | 1/1996 |

OTHER PUBLICATIONS

Derwent-Acc-No. 1996-124175, abstract of Japanese Patent Specification No. JP08-20676A (Jan. 1996).*

* cited by examiner

*Primary Examiner*—Anthony J Green
(74) *Attorney, Agent, or Firm*—Lau & Associates, LLC.

(57) ABSTRACT

An alkoxylpropyl isothiazolinone of formula: $C_6H_6Cl_2NO_2SR$, in which R is $CH_3$, $CH_2CH_3$, $CH(CH_3)_2$, $CH_2CH_2CH_2CH_3$, $CH_2CH_2OCH_3$ or $CH_2CH_2OC_6H_5Cl$. A method for preparing the isothiazolinone by reacting sodium polysulphide with methyl acrylate to obtain dimethyl dithiodipropionate, followed by aminolysis with alkoxyl propylamine to obtain N,N'-dialkoxylpropyldithio-dipropionamide, which is then reacted with sulfuric chloride. The alkoxylpropyl-isothiazolinone of the invention can be used for preparing marine antifouling paint coating as antifoulant, and also used as bactericide.

5 Claims, No Drawings

ALKOXYLPROPYLISOTHIAZOLINONE AND PREPARATION METHOD AND USE THEREOF

BACKGROUND OF THE INVENTION

The present invention relates to a derivate of the isothiazolinone, especially to a alkoxylpropylisothiazolinone compound, a preparing method thereof, and applications thereof for preparing marine antifouling coating and for using as bactericide.

Various marine organisms are adhered to the surfaces of the fishing nets, hull, underwater facilities and the like which were socked in seawater for a long period, and the adhesion of the marine organisms may cause the surfaces defiled, increase surface friction force, and accelerate its erode. The most general method of solving the problem of marine organisms defilement is to coat a coating having antifouling agent. Currently, a antifouling coating comprising organic tin and cuprous oxide are used widely all over the world, namely, a combination of a copolymer of the tributyltin methacrylate and methyl methacrylate and cuprous oxide ($Cu_2O$) is used as an antifouling coating to coat the surfaces of the hull bottom and the like, so as to prevent effectively the harm of the marine organisms. The action mechanism thereof lies in a controlled releasing of the toxinic tributyltin oxide (TBT) and cuprous oxide which has exterminate function to the harmful adhesive substance such as barnacle, ascidian, seaweed and the like which tend to adhere to the surfaces of the hull and marine facilities. But, TBT can also cause sex variation and shell aberration of oyster, boold clam and mussel, and thus may damage severely the marine ecological environment and the marine aquiculture industry. The most noted self-polishing antifouling coating containing TBT is disclosed in EP-A-51930 which is a landmark in the exposure of the TBT copolymer. Thereafter, TBT antifouling coating occupied the antifouling coating market over 20 years. People began to realize that the organic tin compounds have so strong toxicity that they can pollute environment, even influence human health via food chain, till 1987. Due to such reason, it is required to develop a marine antifouling coating free of tin to replace the organic tin marine antifouling coating.

Furthermore, the antiseptics used in current market are various. They may be classified into chlorine-based antiseptic, triazole-based antiseptic and the like. But these antiseptics can cause some problems more or less during using. For example, while the quaternary ammonium salt-based antiseptics have extensive and highly effective sterilization ability, they also have disadvantages such as a high cost, apt to generate foam, and a drug resistance may be generated if they were used alone for a long time. Furthermore, the sterilization ability of such kind of antiseptic may decrease if they are used in water with higher hardness. Other kinds of antiseptics may have features of high toxicity, high residual and the like. However, our government has carried out various active means to cope with the high toxicity, high residual antiseptics, and has inhibited and restricted the vendition and employment thereof specifically. Accordingly, the nuisance-free antiseptics that have high efficiency, low toxicity, low residual or no residual toxicity are required urgently to be developed.

SUMMARY OF THE INVENTION

An object of the present invention is to provide an alkoxylpropylisothiazolinone, which is applied to prepare marine antifouling coating and antiseptics to compensate the demand mentioned above in prior art, and a preparation method thereof.

In order to achieve the object mentioned above, technical solutions used in the present invention are as follows:

An alkoxylpropylisothiazolinone, the molecular formula thereof is $C_6H_6Cl_2NO_2SR$, and the formula thereof is:

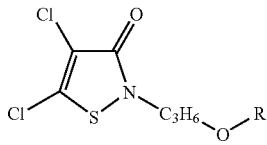

wherein, R is $CH_3$, $CH_2CH_3$, $CH(CH_3)_2$, $CH_2CH_2CH_2CH_3$, $CH_2CH_2OCH_3$ or $CH_2CH_2OC_6H_5Cl$.

The preparation method of the alkoxylpropylisothiazolinone comprises the following steps: reacting sodium polysulphide with methyl acrylate to obtain dimethyl dithiodipropionate, followed by aminolysis with alkoxyl propylamine to obtain N,N'-dialkoxylpropyldithio-dipropionamide, which is then reacted with sulfuric chloride to obtain the alkoxylpropyl-isothiazolinone.

In the preparation method of the alkoxylpropylisothiazolinone, the alkoxylpropylisothiazolinone is 4,5-dichloro-2-methoxypropyl-4-isothiazolin-3-one, 4,5-dichloro-2-ethoxypropyl-4-isothiazolin-3-one, 4,5-dichloro-2-isopropoxypropyl-4-isothiazolin-3 -one, 4,5-dichloro-2-butoxypropyl-4-isothiazolin-3-one, 4,5-dichloro-2-methoxyethoxypropyl-4-isothiazolin-3-one or 4,5-dichloro-2-chlorophenoxyethoxypropyl-4-isothiazolin-3-one.

In the preparation method of the alkoxylpropylisothiazolinone, the alkoxylpropylamine is γ-methoxypropylamine, γ-ethoxypropylamine, γ-isopropoxypropylamine, γ-butoxypropylamine, γ-methoxyethoxypropylamine or γ-phenoxyethoxypropylamine.

The alkoxylpropylisothiazolinone of the present invention is used for preparation of marine antifouling coating.

The marine antifouling coating of the present invention is comprised of resin solution, plasticizer, one or more filler and one or more alkoxylpropylisothiazolinones of the present invention with the percent by weight of 20-60, 1-20, 1-30 and 1-50, respectively, wherein the resin of the resin solution is one or more selected from acrylic resin, chlorinated rubber, zinc acrylate resin and copper acrylate resin, the solvent is one or more selected from ethyl acetate, butyl acetate, xylene, toluene and butanol, and the concentration of the resin solution is in the range of 20%-60%.

The alkoxylpropylisothiazolinone of the present invention may be used as an antiseptic.

The application of the alkoxylpropylisothiazolinone that used as an antiseptic, wherein, the septic is *staphylococcus aureus*, coliform bacteria, or *saccharomyces cerevisiae*.

The alkoxylpropylisothiazolinone of the present invention may be used as an antiseptic for industrial cooling water.

The alkoxylpropylisothiazolinone of the present invention may be used as an antiseptic for the agricultural use.

The merits of the present invention is that the marine coating prepared with alkoxylpropylisothiazolinone of the present invention as the antifouling agent can be degraded and separated rapidly in the environment, and has limited bio-availability to the marine organisms with a little of accumulation in vivo organisms. It has significant antifouling efficiency and a longer lifespan. The preparation of such compound has merits of available raw material, low cost and a higher yield. When using as an antiseptic, the compound of the present invention has many merits such as high efficiency, broad spectrum, low toxicity, low residual and the like. The compound of the present invention can be degraded rapidly in the environment due to their bioactivity, with low toxicity or nontoxicity substance releasing, thus may not render the environment pollution.

DETAILED DESCRIPTION OF THE INVENTION

1. Preparation of Dimethyl Dithiodipropionate

In a 500 ml three neck flask equipped with a stirrer, a condenser and a thermometer, 200 ml 10% (percentage by weight, hereinafter is the same) NaHCO$_3$ solution and 21.7 g (0.25 mol) methyl acrylate were added sequentially, then the system was cooled to −5-10° C. Keeping under the temperature, a cooling sodium polysulphide (0.19 mol, counted by Na$_2$S) solution was dropped during 0.5-2 hours. After the dropwise addition, ice water bath was removed. The mixture was left standing under the room temperature for 5-6 hours. Then the reaction was over. The obtained mixture was allowed to stand and separate into two layers. The water layer was removed. A 120 ml (1 mol/L) Na$_2$SO$_3$ solution was added to the oil layer. The mixture then reacted continuously for 2-5 hours under the temperature of 50° C. until the reaction was over. The resulting mixture was again allowed to stand and separate into layers. Then the water layer was removed, and the oil layer was washed with water. 26.8 g light yellow oily substance was obtained by vacuum distilling, the yield is 89.3%, the boiling point is 182-185° C./7 mmHg.

2. Preparation of N,N'-Dimethoxylpropyldithiodipropionamide

In a 500 ml three neck flask equipped with a stirrer, a condenser and a thermometer, 26.7 g (0.3 mol) γ-methoxypropylamine, 2.5 ml triethylamine are added sequentially, the temperature of the reaction system was controlled to −5-5° C. and maintained. Then 23.8 g (0.1 mol) β-dimethyl dithiodipropionate prepared by the front step was dropped during 0.5-1.5 hours. After dropwise addition, the ice water bath was removed. The reaction was left standing for 24 hours under the room temperature, and then the reaction was over. A golden solid was obtained. And a light yellow solid product was yielded by vacuum filtration. After dried it was recrystallized with anhydrous alcohol. 24.1 g white chip crystal was obtained, and the yield is 68.4%, the boiling point is 103.3-105.1° C.

N,N'-diethoxylpropyldithiodipropionamide, N,N'-diisopropoxydithiodipropionamide, N,N'-dibutoxypropyldithiodipropionamide, N,N'-dimethoxyethoxypropyldithiodipropionamide or N,N'-diphenoxyethoxypropyldithiodipropionamide can be obtained, respectively, when the γ-methoxypropylamine in the embodiment is replaced with γ-ethoxypropylamine, γ-isopropoxypropylamine, γ-butoxypropylamine, methoxyethoxypropylamine or γ-phenoxyethoxypropyl-amine.

3. Preparation of 4,5-dichloro-2-methoxypropyl-4-isothiazolin-3-one

In a 250 ml three neck flask equipped with a stirrer, a condenser and a thermometer, 175 ml ethyl acetate and 18.0 g (0.05 mol) N,N'-diethoxylpropyldithiodipropionamide are added sequentially. Keeping the temperature of the system to −10-5° C., 40.0 g (0.3 mol) sulfuric chloride was dropped during 3 hours. The reaction is kept to be continued for 3 hours under the temperature, and then the temperature of the reaction system was raised slowly to the room temperature. The mixture was allowed to react for another 3 hours in the water bath under the temperature of 30-35° C. until the reaction was over. The resulting solution was added 50 ml water and then oscillated for 3 minutes. The resulting mixture was allowed to stand and separated to two layers. The organic phase was dried over anhydrous magnesium sulfate (15.0 g) for 15 minutes, and then filtrated. The solvent was removed from the filtrate by decompression via spin-evaporimeter. 15.4 g yellow thick liquid was obtained, the primary yield is 63.9%, the yield of the pure product separated by column is 56.6%.

4,5-dichloro-2-ethoxypropyl-4-isothiazolin-3-one, 4,5-dichloro-2-isopropoxy propyl-4-isothiazolin-3-one, 4,5-dichloro-2-butoxypropyl-4-isothiazolin-3-one, 4,5-dichloro-2-methoxyethoxypropyl-4-isothiazolin-3-one, or 4,5-dichloro-2-phenoxyethoxypropyl-4-isothiazolin-3-one can be obtained respectively, when the N,N'-dimethoxylpropyldithiodipropionamide in the embodiment is replaced with N,N'-diethoxylpropyldithiodipropionamide, N,N'-isopropoxypropyldithiodipropionamide, N,N'-diisopropoxydithiodipropionamide, N,N'-dibutoxypropyldithiodipropionamide, N,N'-dimethoxyethoxy propyldithiodipropionamide or N,N'-diphenoxyethoxy propyldithiodipropionamide.

The resulting product is characterized by nuclear magnetic resonance ($^1$H NMR) method. The characteristic peak thereof is shown in the following table:

| compound | Solvent | H atom serial number | δ value | Peak shape |
|---|---|---|---|---|
| 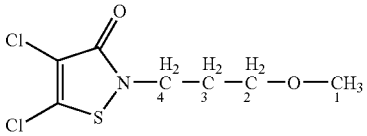4,5-dichloro-2-methoxypropyl-4-isothiazolin-3-one | CDCl$_3$ | 1<br>2<br>3<br>4<br>5 | 3.3506<br>3.4147<br>1.9839<br>3.9073<br>6.2644 | S<br>T<br>M<br>T<br>S |
| 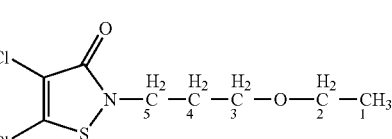4,5-dichloro-2-ethoxypropyl-4-isothiazolin-3-one | CDCl$_3$ | 1<br>2, 3<br>4<br>5 | 1.2139<br>3.4662<br>1.9759<br>3.9243 | T<br>M<br>M<br>T |

-continued

| compound | Solvent | H atom serial number | δ value | Peak shape |
|---|---|---|---|---|
| 4,5-dichloro-2-isopropoxypropyl-4-isothiazolin-3-one | $CDCl_3$ | 1, 2 | 1.1683 | D |
| | | 3 | 3.5661 | M |
| | | 4 | 3.4531 | T |
| | | 5 | 1.9593 | M |
| | | 6 | 3.9195 | T |
| 4,5-dichloro-2-butoxypropyl-4-isothiazolin-3-one | $CDCl_3$ | 1 | 0.9327 | T |
| | | 2 | 1.3899 | M |
| | | 3 | 1.5688 | M |
| | | 4, 5 | 3.4354 | M |
| | | 6 | 1.9723 | M |
| | | 7 | 3.9165 | T |
| 4,5-dichloro-2-methoxyethoxypropyl-4-isothiazolin-3-one | $CDCl_3$ | 1 | 3.3970 | S |
| | | 2 | 3.5160 | T |
| | | 3 | 3.5569 | M |
| | | 4 | 3.5929 | M |
| | | 5 | 2.0046 | M |
| | | 6 | 3.9243 | T |
| 4,5-dichloro-2-chlorophenoxythoxypropyl-4-isothiazolin-3-one | $CDCl_3$ | 1 | 4.1121 | T |
| | | 2 | 1.9820 | M |
| | | 3 | 3.7915 | M |
| | | 4 | 3.8571 | M |
| | | 5 | 3.8342 | M |
| | | 6, 10 | 6.8591 | M |
| | | 7, 9 | 7.2409 | T |

INDUSTRIAL APPLICATION

The alkoxylpropylisothiazolinone is used as antifouling for preparation of the marine antifouling coating:

The compound of the present invention is used for preparation of the marine antifouling coating which is comprised of resin solution, plasticizer, one or more filler and one or more compound of the present invention in the percent by weight of 20-60, 1-20, 1-30 and 1-50. Wherein the concentration range of the resin solution is 20%-60% (percentage by weight, hereinafter is the same). The acrylic resin solution which has film forming function such as chlorinated rubber solution, zinc acrylate resin solution and copper acrylate resin solution can be used; the solvent may be ethyl acetate, butyl acetate, xylene, toluene and butanol; the plasticizer may be vaseline, clorafin, dibutyl phthalate or dioctyl phthalate; the filler may be red iron oxide, talcum powder, titanium dioxide, gas phased silicon dioxide or zinc oxide. The antifouling coating of the present invension is prepared as follows: a mixture of 50 g acrylic resin in butyl acetate solution with the concentration of 40%, 2.5 g clorafin, 12 g red iron oxide, 2.5 g gas phase silicon dioxide, 33 g 4,5-dichloro-2-dibutoxy-propyl-4-isothiazolin-3-one was oscillated for 2 hours in the beaded paint oscillator having a glass bead, then the mixture was filtrated by a filter with 100 screen mesh. To measure the antifouling performance of the resulting antifouling coating, referring to Chinese National Standard "Testing method of the antifouling coating sample board socked in the shallow sea" (GB 5370-85), the obtained antifouling coating was coated on the mild steel testing sample board, with length of 250 mm, width of 150 mm, thickness of 2 mm, and the board was held by rectangular batten having grooves fixed with iron bolt at its both ends. The testing sample board was hung at the submerged cages culture area of Xunshan town in Rongcheng city for 2 years. A significant experimental result was achieved, as shown in the following table.

| | 6 months | 12 months | 24 months |
|---|---|---|---|
| blank sample board | 20 | 40 | 100 |
| sample board coated with antifouling coating | 0 | 0 | 3 |

Note: 0, 3, 20, 40, 100 represent the adhesion area percent of the marine organisms on the sample boards.

The alkoxylpropylisothiazolinone of the present invention used as antiseptic:

The lowest bacteriostasis concentration of the six kinds of the alkoxylpropylisothiazolinone of the present invention is measured through the tube double dilution method. In a Φ18× 180 mm tube, 5 ml aseptic culture medium was added, then 50 μl bacteria suspended liquid of coliform was injected to prepare culture solution of beef extract peptone having bacteria concentration of $10^7$ cfu/ml, then 50 μl tetrahydrofuran solution containing 4,5-dichloro-2-isopropoxypropyl-4-isothiazolin-3-one with the concentration of 2 μg/ml, 4 μg/ml, 8 μg/ml, 16 μg/ml, 32 μg/ml were added respectively. After cultured for 24 hours under a constant temperature of 37° C., the lowest bacteriostasis concentration of 4,5-dichloro-2-isopropoxypropyl-4-isothiazolin-3-one against coliform bacteria was measured. The result is 8 μg/ml (the cfu is a colong forming unit, 1 cfu refer to one single colong formed on the agar plate after being cultured).

When the coliform bacteria of the present invention is replaced with *saccharomyces cerevisiae* or *staphylococcus aureus*, and the 4,5-dichloro-2-isopropoxypropyl-4-isothiazolin-3-one is replaced with 4,5-dichloro-2-methoxy-propyl-4-isothiazolin-3-one, 4,5-dichloro-2-ethoxypropyl-4-isothiazolin-3-one, 4,5-dichloro-2-butoxypropyl-4-isothiazolin-3-one, 4,5-dichloro-2-methoxyethoxypropyl-4-isothiazolin-3-one, or 4,5-dichloro-2-chlorophenoxyethoxypropyl-4-isothiazolin-3-one, a considerable experimental results are also received, which are shown in the following table.

The lowest bacteriostasis concentration of six kinds of alkoxylpropyliso-thiazolinone (unit:μg/ml)

| compound | staphylococcus aureus | coliform bacteria | saccharomyces cerevisiae |
|---|---|---|---|
| 4,5-dichloro-2-methoxypropyl-4-isothiazolin-3-one | 32 | 4 | 16 |
| 4,5-dichloro-2-ethoxypropyl-4-isothiazolin-3-one | 16 | 4 | 8 |
| 4,5-dichloro-2-isopropoxypropyl-4-isothiazolin-3-one | 16 | 8 | 8 |
| 4,5-dichloro-2-butoxypropyl-4-isothiazolin-3-one | 8 | 4 | 4 |
| 4,5-dichloro-2-methoxyethoxypropyl-4-isothiazolin-3-one | 16 | 16 | 16 |
| 4,5-dichloro-2-chlorophenoxyethoxypropyl-4-isothiazolin-3-one | 16 | 8 | 8 |

The compound of the present invention may be used to control and sterilize alga, fungi and bacteria in the industrial cooling water system. First, chlorine was stopped adding into the circulating water system for 3 days before administration. The total amount of the heterotrophic bacteria in the circulating water was raised, and then the 4,5-dichloro-2-methoxy-ethoxypropyl-4-isothiazolin-3-one was thrown in, while the discharge of the water was stopped. The amount of the heterotrophic bacteria in water and the sterilization rate was measured at 4 hours, 12 hours, 24 hours, 36 hours after the medicament was added. The test result is shown in the following table. It indicates that the compound of the present invention can control and sterilize effectively the heterotrophic bacteria in the industry cooling water water.

| the time of sterilization (h) | the concentration of the medicament (mg/L) | the amount of the heterotrophic bacteria (number/mL) | | the rate of sterilization % |
|---|---|---|---|---|
| | | the request of standardization design | virtual result | |
| before the medicament is added | 0 | $5 \times 10^5$ | $3.0 \times 10^7$ | 0 |
| 4 | 50 | $5 \times 10^5$ | $2.0 \times 10^5$ | 99.33 |
| 12 | 50 | $5 \times 10^5$ | $4.0 \times 10^4$ | 99.87 |
| 24 | 50 | $5 \times 10^5$ | $3.0 \times 10^4$ | 99.90 |
| 36 | 50 | $5 \times 10^5$ | $3.3 \times 10^4$ | 99.89 |

When the 4,5-dichloro-2-methoxyethoxypropyl-4-isothiazolin-3-one of the present embodiment is replaced with 4,5-dichloro-2-methoxylpropyl-4-isothiazolin-3-one, 4,5-dichloro-2-ethoxylpropyl-4-isothiazolin-3-one, 4,5-dichloro-2-isopropoxy-propyl-4-isothiazolin-3-one, 4,5-dichloro-2-butoxypropyl-4-isothiazolin-3-one or 4,5-dichloro-2-phenoxyethoxypropyl-4-isothiazolin-3-one, the microorganism in industry cooling water can also be controlled and sterilized effectively.

Through the measuremémt of drug action and field test, the alkoxypropylisothiazolinone of the present invention is proved to have considerable sterilization and prophylaxis function to wheat scab and leaf spot of beet. Otherwise, it has also a good prevent function to the apple ring rot, tomato gray mold and cotton soreshin. For example, when the 4,5-dichloro-2-isopropoxypropyl-4-isothiazolin-3-one is used as bactericide, it is merely required 39 g pure medicament per mu (¹⁄₁₅ of a hectare) with the concentration of 250 ppm to control the leaf spot of bee, and the efficiency of the prevention and cure is up to 75.0%.

When the 4,5-dichloro-2-butoxypropyl-4-isothiazolin-3-one of the present embodiment is replaced with 4,5-dichloro-2-dimethoxyethoxypropyl-4-isothiazolin-3-one, 4,5-dichloro-2-ethoxylpropyl-4-isothiazolin-3-one, 4,5-dichloro-2-isopropoxy-propyl-4-isothiazolin-3-one, 4,5-dichloro-2-methoxyethoxylpropyl-4-isothiazolin-3-one or 4,5-dichloro-2-diphenoxyethoxypropyl-4-isothiazolin-3-one, a considerable effect of the prevention and cure can also be obtained.

What is claimed is:

1. A method of preparing a compound of a formula:

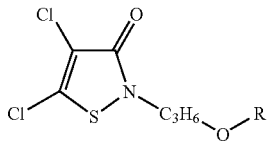

wherein, R is $CH_3$, $CH_2CH_3$, $CH(CH_3)_2$, $CH_2CH_2CH_2CH_3$, $CH_2CH_2OCH_3$ or $CH_2CH_2OC_6H_5Cl$ comprising reacting sodium polysulphide with methyl acrylate to obtain dimethyl dithiodipropionate, followed by aminolysis with alkoxyl propylamine to obtain N,N'-dialkoxylpropyldithiodipropionamide, which is then reacted with sulfuric chloride to obtain the alkoxyipropyl-isothiazolinone.

2. The method of claim 1, wherein the alkoxyipropylamine is γ-methoxypropylamine, γ-ethoxypropylamine, γ-isopropoxypropylamine, γ-butoxypropylamine, γ-methoxyethoxypropylamine or γ-phenoxyethoxypropylamrne.

3. An antifouling coating composition comprised of resin solution, a plasticizer, filler, and a compound having a formula:

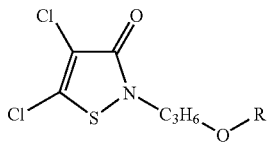

wherein, R is CH$_3$, CH$_2$CH$_3$, CH(CH$_3$)$_2$, CH$_2$CH$_2$CH$_2$CH$_3$, CH$_2$CH$_2$OCH$_3$ or CH$_2$CH$_2$OC$_6$H$_5$Cl, wherein the percent by weight is 20-60, 1-20, 1-30 and 1-50, respectively.

4. The antifouling coating of claim 3 wherein the resin is acrylic resin, chlorinated rubber or zinc diacrylate resin; a solvent is ethylacetate, butyl acetate, xylene, toluene or butanol, and an amount of resin comprises from 20-60% of solvent by weight.

5. method for inhibiting fouling of surfaces exposed to seawater by marine organisms comprising;
coating a surface to be exposed to marine organisms with a composition of resin solution, a plasticizer, filler and a compound having a formula

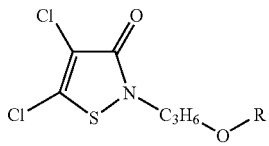

wherein, R is CH$_3$, CH$_2$CH$_3$, CH(CH$_3$)$_2$, CH$_2$CH$_2$CH$_2$CH$_3$, CH$_2$CH$_2$OCH$_3$ or CH$_2$CH$_2$OC$_6$H$_5$Cl and wherein the percent by weight is 20-60, 1-20, 1-30 and 1-50, respectively.

* * * * *